US009412558B2

United States Patent
Van Dyck et al.

(10) Patent No.: US 9,412,558 B2
(45) Date of Patent: Aug. 9, 2016

(54) HIGH-RESOLUTION AMPLITUDE CONTRAST IMAGING

(71) Applicants: UNIVERSITEIT ANTWERPEN, Antwerpen (BE); FEI COMPANY, Hillsboro, OR (US)

(72) Inventors: Dirk Van Dyck, Aartselaar (BE); Uwe Lucken, Suedbrookmerland (DE); Holger Stark, Waake (DE); Sara Bals, Antwerpen (BE)

(73) Assignees: UNIVERSITEIT ANTWERPEN, Antwerpen (BE); FEI COMPANY, Hillsboro, OR (US)

( * ) Notice: Subject to any disclaimer, the term of this patent is extended or adjusted under 35 U.S.C. 154(b) by 0 days.

(21) Appl. No.: 14/767,796

(22) PCT Filed: Feb. 14, 2014

(86) PCT No.: PCT/EP2014/052973
§ 371 (c)(1),
(2) Date: Aug. 13, 2015

(87) PCT Pub. No.: WO2014/125098
PCT Pub. Date: Aug. 21, 2014

(65) Prior Publication Data
US 2015/0380211 A1    Dec. 31, 2015

(30) Foreign Application Priority Data

Feb. 14, 2013  (GB) .................................. 1302624.0

(51) Int. Cl.
*H01J 37/26*    (2006.01)
*H01J 37/06*    (2006.01)
(Continued)

(52) U.S. Cl.
CPC .............. *H01J 37/265* (2013.01); *G01N 23/04* (2013.01); *H01J 37/06* (2013.01); *H01J 37/244* (2013.01);
(Continued)

(58) Field of Classification Search
USPC .................... 250/306, 307, 309–311, 339.01, 250/339.06, 370.08, 397, 492.3, 559.05, 250/559.07, 526
See application file for complete search history.

(56) References Cited

U.S. PATENT DOCUMENTS 3,660,657 A * 5/1972 Brookes .................. H01J 37/20
250/311
5,134,288 A * 7/1992 Van Dijck ............. H01J 37/222
250/307
(Continued)

FOREIGN PATENT DOCUMENTS

WO    2013012041 A1    1/2013

OTHER PUBLICATIONS

Forbes et al., "Thermal Diffuse Scattering in Transmission Electron Microscopy," Ultramicroscopy, 2011, pp. 1670-1680, vol. 111.
(Continued)

*Primary Examiner* — Bernard Souw
(74) *Attorney, Agent, or Firm* — Workman Nydegger

(57) ABSTRACT

A method for performing high resolution electron microscopy of a soft matter object is described. The method comprises irradiating a soft matter object using an electron microscope having a spherical aberration correction with a substantially constant transfer function in a frequency band of thermal diffuse scattered electrons scattered at the soft matter object. The method comprises detecting the thermal diffuse scattered (TDS) electrons scattered at the soft matter, and using the detected thermal diffuse scattered electrons for deriving therefrom an image of the soft matter object.

20 Claims, 8 Drawing Sheets

(51) Int. Cl.
*G01N 23/04* (2006.01)
*H01J 37/244* (2006.01)

(52) U.S. Cl.
CPC ......... *H01J 37/26* (2013.01); *G01N 2223/0565* (2013.01); *G01N 2223/612* (2013.01); *H01J 2237/063* (2013.01); *H01J 2237/1534* (2013.01); *H01J 2237/2602* (2013.01); *H01J 2237/2614* (2013.01)

(56) References Cited

U.S. PATENT DOCUMENTS

| | | | | |
|---|---|---|---|---|
| 5,432,347 | A * | 7/1995 | Coene | G03H 5/00 250/307 |
| 5,866,905 | A * | 2/1999 | Kakibayashi | G01N 23/046 250/311 |
| 6,051,834 | A * | 4/2000 | Kakibayashi | H01J 37/28 250/311 |
| 8,878,130 | B2 | 11/2014 | Inada et al. | |
| 9,029,767 | B2 * | 5/2015 | Bischoff | H01J 37/153 250/311 |
| 2006/0255273 | A1 | 11/2006 | Kasai et al. | |
| 2009/0078868 | A1 * | 3/2009 | de Jonge | H01J 37/26 250/310 |
| 2011/0233403 | A1 | 9/2011 | Own et al. | |
| 2013/0043386 | A1 | 2/2013 | Yamazaki | |
| 2014/0138542 | A1 | 5/2014 | Inada et al. | |

OTHER PUBLICATIONS

Great Britain Search Report for corresponding Great Britain Application No. GB1302624.0, Aug. 23, 2013.
Hu et al., "Beam Alignment and Related Problems of Spherical Aberration Corrected High-Resolution TEM Images," Journal of Electron Microscopy, 2000, pp. 651-656, vol. 49, No. 5.
International Search Report for corresponding International PCT Application No. PCT/EP2014/052973, Apr. 15, 2014.
Lichte, "Optimum Focus for Taking Electron Holograms," Ultramicroscopy, 1991, pp. 13-22, vol. 38.
Liu et al., "Imaging with High-Angle Scattered Electrons and Secondary Electrons in the STEM," Ultramicroscopy, 1991, pp. 50-71, vol. 37.
Wang et al., "Simulating High-Angle Annular Dark-Field Stem Images Including Inelastic Thermal Diffuse Scattering," Ultramicroscopy, 1989, pp. 437-454, vol. 31.
Wang et al., "Dynamic Theory of High-Angle Annular-Dark-Field Stem Lattice Images for a Ge/Si Interface," Ultramicroscopy, 1990, pp. 275-289, vol. 32.
Wang, "Thermal Diffuse Scattering in Sub-Angstrom Quantitative Electron Microscopy—Phenomenon, Effects and Approaches," Micron, 2003, pp. 141-155, vol. 34.

* cited by examiner

HIGH-RESOLUTION AMPLITUDE CONTRAST IMAGING

FIELD OF THE INVENTION

The invention relates to the field of imaging objects. More specifically it relates to a method and system for imaging soft matter objects such as biological objects using electron microscopy.

BACKGROUND OF THE INVENTION

In the quest for the full understanding of life processes at the cellular level, high resolution biological imaging plays an important role. Many proteins are considered modules that are used a multiple of times in the formation of different complexes. For most of the complexes the function is as yet unknown. However it is thought that they participate in key processes in the living cell and that an understanding of the structure and the dynamics of the constituent proteins is required as a necessary step towards a full understanding of life processes at the cellular level. The large size of the complexes formed in multiple associations and their likely dynamical variability in the functional context takes most of these complexes out of the reach of X-ray crystallography and leaves Cryo-electron microscopy as one of the few techniques of structural investigation. Single particle techniques in particular are preferred since they leave molecular interactions constrained.

In the world of single particle cryo-EM, the credo is that biological objects are phase objects that can only be studied using phase contrast microscopy. The usual way to get phase contrast in electron microscopy is by compensating the spherical aberration Cs with negative defocus (Scherzer focus) so as to create a passband of spatial frequencies for which the phase shift is approximately equal to 90°. However in such passband the phase transfer at the low spatial frequencies is very poor which is a problem for biological objects where the information about the shape is in this range.

A possible solution is to develop a phase plate that is able to shift the phase of the central beam over 90° with respect to the diffracted beams. However despite all the efforts that have been invested in the development of phase plates thus far no clear demonstration of high resolution imaging with phase plates has yet been demonstrated.

A more practical way to obtain more phase contrast in the low spatial frequency range is by using a very large defocus (of the order of 2 micrometer) and by compensating for the missing gaps by combining several defocus values and assuming that the imaging is linear. But the drawback of a strong defocus is that at large defocus, the spatial incoherence of the microscope strongly limits the resolution to the order of about 4 Angstrom. Therefore it is generally believed that the use of a Cs corrector, although very successful in HREM of inorganic materials is of limited value for single-particle Cryo-EM.

SUMMARY OF THE INVENTION

It is an object of the present invention that a good imaging techniques and systems suitable for soft matter, e.g. biological objects, are provided.

It is an advantage of embodiments of the present invention that it is realized that spherical aberration (Cs) corrected high resolution electron microscopy can be used for imaging soft matter, e.g. biological material.

It has surprisingly been found that use can be made of thermal diffuse scattered (TDS) electrons of soft matter such as biological objects. It was found that the signal of TDS electrons of soft matter can be large because it is not only function of the atomic number of the atoms but also of the mean square displacement (MSD), which depends on the binding energy.

It is an advantage of embodiments according to the present invention that methods and systems are provided for performing high resolution electron microscopy imaging suitable for soft matter, e.g. biological objects, that make use of large angle scattered electrons, e.g. mainly comprising thermal diffuse scattered (TDS) electrons.

It is an advantage of embodiments of the present invention that TDS scattering is incoherent and thus does not interfere with the central beam. Therefore it generates amplitude contrast that can be imaged at the highest resolution, e.g. with a flat transfer function (phase shift zero) that can be reached with a spheric abberations (Cs) corrector and e.g. with a very small under focus.

It is an advantage of embodiments of the present invention that methods and systems are provided that provide optimum detection at a spatial frequency of around 1/Angström, which is exactly the range in which a flat passband can be reached with a spheric aberrations (Cs) corrector.

It is an advantage of embodiments of the present invention that the TDS signal is easy to interpret and linear in the "mass-thickness" so that is it very suited for tomography.

It is an advantage of embodiments of the present invention that an annular dark field objective aperture that is specially optimized for this imaging technique can be used for selecting the thermal diffuse scattered electrons. In a sense the method is then comparable to HAADF STEM but with all the advantages of HREM.

The above objective is accomplished by a method and device according to the present invention.

The present invention relates to a method for performing high resolution electron microscopy of an object, the method comprising irradiating an object using an electron microscope having a spherical aberration correction with a substantially constant transfer function in a frequency band of thermal diffuse scattered electrons scattered at the object at atomic level resolution, characterized in that the method comprises detecting the thermal diffuse scattered electrons scattered at the object, and deriving an image of the soft matter object based on the detected thermal diffuse scattered electrons.

Where in embodiments of the present invention reference is made to a substantially constant transfer function, reference is made to situations wherein deviations of the average are in the order of micrometers or lower.

According to embodiments of the present invention, the objects under study may be soft matter objects, although embodiments are not limited thereto. It is an advantage of embodiments of the present invention that proteins can be investigated using the methods disclosed. It thereby is an advantage that the thermal diffusive scattering is around 1 Angström, which is within the reach of a Cs corrected electron microscope.

The method advantageously also can be used for studying polymers. The methods are nevertheless also applicable for inorganic materials.

It is an advantage of embodiments of the present invention that use is made of thermal diffuse scattered electrons scattered at the object for imaging the object. The object may be soft matter. In one embodiment it may be proteins. Embodiments of the present invention take advantage of the fact that the inventors have realized that thermal diffuse scattering is useful when imaging soft matter, e.g. biological objects at atomic level resolution.

The frequency band of thermal diffuse scattered electrons scattered at the soft matter object may comprise the range between 0.5 Å$^{-1}$ and 1.0 Å$^{-1}$. The irradiating furthermore may be performed using a small defocus. The irradiating may be performed using a small under focus.

The aberration correction Cs can be in the order of a few micrometer and the corresponding defocus D can be in the order of a few nanometer. Values for aberration correction and defocus may e.g. be selected as follows. For a resolution R one wants to reach, one can determine the aberration correction as $(1.6 R)4/((L)3)$ with L being the wavelength. The corresponding defocus D can then be determined as 1,2 times the square root of Cs·L.

The irradiating may be performed using an annular dark field objective aperture.

Imaging using an annular dark field objective aperture may comprise imaging using an annular dark field objective aperture having a substantially annular ring shape, wherein the annular ring shape has an inner and an outer radius, the inner and the outer radius selected corresponding with the frequency band of the thermal diffuse scattered of electrons scattered at a biological object.

The frequency band may be between 0.5 Angstrom (−1) and 1 Angstrom (−1). In one embodiment, the frequency band may be selected as being between 0.5/σ and 1/σ with σ the average thermal displacement of the atom.

The soft matter object may be a biological object.

Performing high resolution electron microscopy may comprise performing tomography.

Deriving an image may comprise adding the incoherent contribution of each atom independently to the final image.

Deriving an image of the soft matter object based on the detected thermal diffuse scattered electrons may comprise deriving independent sub-images based on the incoherent contribution of each atom.

The method may comprise tomographic imaging of particles of a three dimensional soft matter object, whereby particles having a different depth position in the object with respect to the imaging system resulting in a defocus smaller than a predetermined value, are image in the same imaging step using the same imaging conditions.

The method may comprise imaging particles having a different depth position in the object with respect to the imaging system resulting in a defocus larger than a predetermined value, in a separate imaging step using different imaging conditions taking into account the different defocus value.

The present invention also relates to a system for performing high resolution electron microscopy of a soft matter object at atomic level resolution, the system comprising a spherical aberration corrector inducing in the system a substantially constant transfer function in a frequency band of thermal diffuse scattered electrons scattered at the soft matter object, characterized in that the system also comprises a detector adapted for detecting the thermal diffuse scattered electrons scattered at the soft matter and an image processor for deriving an image of the soft matter object based on the detected thermal diffuse scattered electrons.

The electron microscope may have a substantially constant transfer function in range between 0.5 Å$^{-1}$ and 1.0 Å$^{-1}$.

The electron microscope furthermore may comprise an annular dark field objective aperture.

The annular dark field objective aperture may have an annular ring shape with an inner radius and an outer radius, the inner and the outer radius being selected corresponding with the frequency band of the thermal diffuse scattered of electrons scattered at a soft matter object.

The present invention also relates to an annular dark field objective aperture for use in an electron microscopy system, the annular dark field objective aperture having an annular ring shape with an inner radius and an outer radius, the inner and the outer radius selected corresponding with the frequency band of the thermal diffuse scattered of electrons scattered at a soft matter object.

The present invention furthermore relates to the use of a system as described above, for imaging a soft matter object.

The present invention also relates to the use of a system as described above for a biological object.

The present invention furthermore relates to an electron microscope image obtained using a method as described above.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
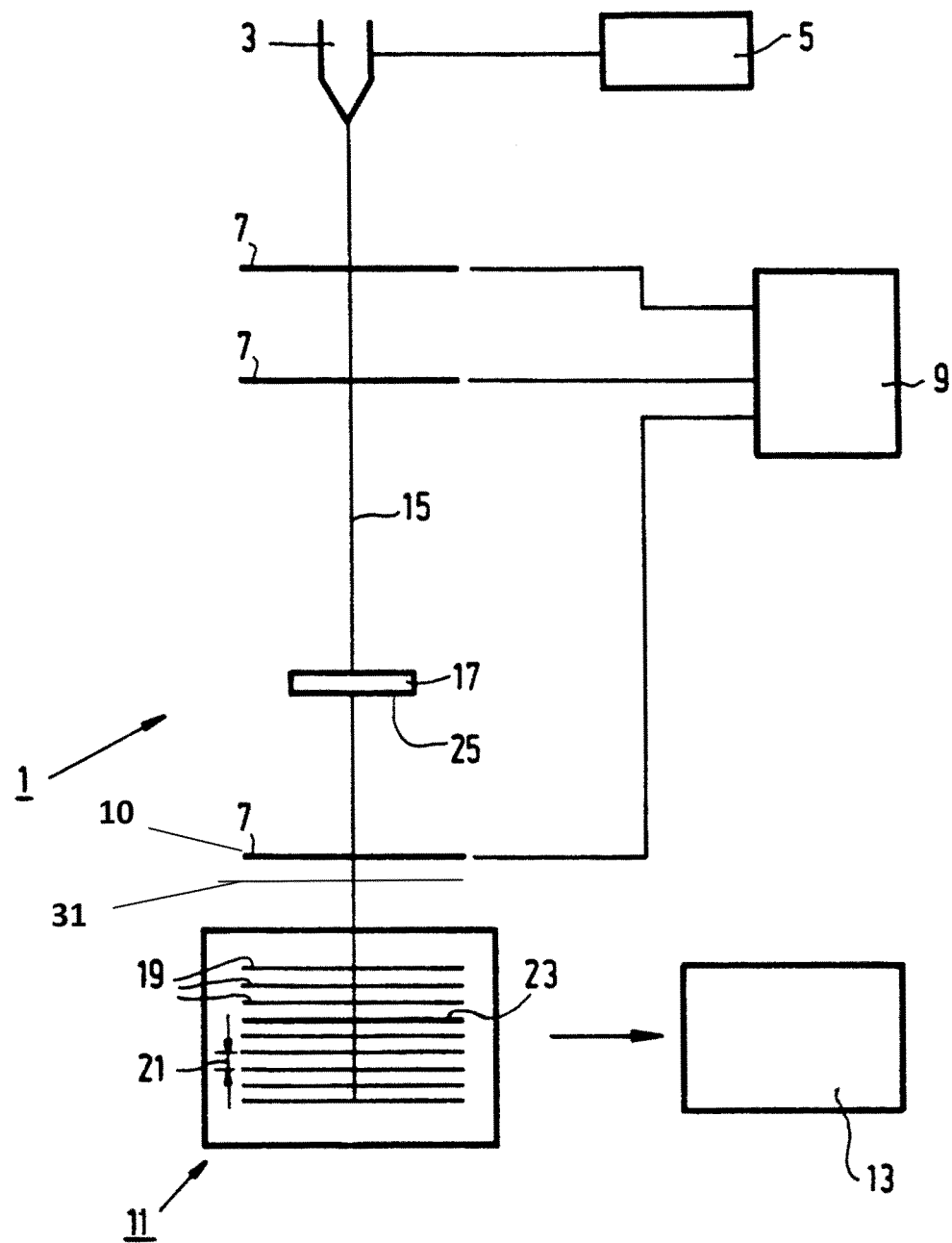
FIG. 1 illustrates a system for electron microscopy according to an embodiment of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Whereas in embodiments of the present invention reference is made to a "Cs corrected" electron microscope, reference is made to an electron microscope corrected for spherical aberration Cs using a Cs corrector. Such a Cs corrector produces negative spherical aberration to combine with the positive aberration of the objective lens to result in an electron microscope having reduced or being substantially free of spherical aberration.

Whereas in embodiments of the present invention reference is made to the atomic level or Angstrom level, sizes envisaged are in the range of 0.1 to 10 Angstrom, or more preferably in the range of 0.1 to 5 Angstrom even more preferably 0.1 to 3 Angstrom.

In a first aspect, the present invention relates to a method for performing high resolution electron microscopy of a soft matter object. Where in embodiments of the present invention reference is made to soft matter, the latter may include e.g. biological objects or objects comprising biological matter, such as for example proteins or larger biological structures consisting of proteins such as ribozomes etc. It is an advantage of embodiments of the present invention that proteins having a size in the range 10 nm to 1000 nm or larger which are difficult to characterize with other techniques, can be studied using embodiments of the present invention. The methods also are advantageously usable for high resolution imaging, e.g. for imaging at the atomic level. According to embodiments of the present invention, the method comprises irradiating a soft matter object using an electron microscope having a spheric aberration correction with a substantially constant transfer function in a frequency band of thermal diffuse scattered electrons scattered at the soft matter object. Such a frequency band may for example comprise part or all of or be included in the range the range between 0.5 $\text{Å}^{-1}$ and 1.0 $\text{Å}^{-1}$. According to embodiments of the present invention, thermal diffuse scattered (TDS) electrons scattered at the soft matter are then detected for using these in the imaging technique. Embodiments of the present invention take advantage of the fact that it was realized that the thermal diffuse scattering comprises information useful for deriving based thereon images of the objects studied. Rather than reducing or avoiding the thermal diffuse scattering, embodiments of the present invention furthermore comprise deriving an image of the soft matter object based on these detected thermal diffuse scattered electrons. It thereby is an advantage that the different atoms of the object all have an incoherent scattering, resulting in the fact that deriving an image typically may comprise adding the incoherent contribution of each atom independently to the final image. The interpretation of the detected signals towards images therefore also becomes more feasible. Different sub-images representing different atoms may be derived and the final image may be a combination of the different sub-images detected.

For obtaining a substantially constant transfer function, the method also may comprise applying a small defocus, e.g. an under focus.

In a particular embodiment, the method comprises, during said irradiating, using a means for selecting the thermal diffuse scattered electrons in the detection process. The method may for example comprise using an annular dark field objective aperture. Such an aperture may be an aperture having a substantially annular ring shape, wherein the annular ring shape has an inner and an outer radius appropriately selected so that electrons from within the frequency band of the thermal diffuse scattered of electrons scattered at a biological object are selected and subsequently detected.

The method as described above may advantageously be applied for performing tomographic imaging. In other words, the method can be used for imaging a three dimensional object. In one embodiment, the particles having a different depth position in the object with respect to the imaging system resulting in a defocus smaller than a predetermined value, can be image in the same imaging step using the same imaging conditions. In other embodiments, the particles having a different depth position in the object with respect to the imaging system resulting in a defocus larger than a predetermined value, will be imaged or derived in a separate imaging step using different imaging conditions taking into account the different defocus value. Features and advantages thereof will be discussed further below, embodiments of the present invention not being limited thereto.

In one aspect, the present invention also relates to system for performing high resolution electron microscopy of a soft matter object. Such a system typically also may be referred to as an electron microscope. Although embodiments of the present invention are not limited to particular types of electron microscopes, the present invention advantageously relates to high resolution electron microscopes. According to embodiments of the present invention, the electron microscope comprises a spherical aberration Cs corrector for correcting for spherical aberration. The corrector thereby is adapted for inducing in the system a substantially constant transfer function in a frequency band of thermal diffuse scattered electrons scattered at the soft matter object. In one example, the transfer function is substantially constant in a range between 0.5 Å$^{-1}$ and 1.0 Å$^{-1}$. As indicated above, such a Cs corrector produces negative spherical aberration to combine with the positive aberration of the objective lens to result in an electron microscope having reduced or being substantially free of spherical aberration. An example of a Cs corrector may e.g. be a quadrupole-octupole lens or a hexapole lens.

According to embodiments of the present invention, the system also comprises a detector or detection system adapted for detecting the thermal diffuse scattered electrons scattered at the soft matter. The system furthermore comprises an image processor, also referred to as image processing system, for deriving an image of the soft matter object based on the detected thermal diffuse scattered electrons. Such a processor may in some embodiments be adapted for deriving the image by adding the incoherent contributions of each atom independently to the final image. The processor thus may derive different sub-images each representative for separate atoms. The system according to embodiments of the present invention furthermore may comprise standard and optional features, as illustrated by way of example, in FIG. 1, embodiments not being limited thereto.

FIG. 1 illustrates a schematic example of an electron microscope according to an embodiment of the present invention, although methods and systems according to embodiments of the present invention are not limited thereby. The high-resolution electron microscope 1, which is diagrammatically shown in FIG. 1 comprises an electron source 3 which is fed by a high-voltage generator 5, and also comprises a number of lenses which are fed by a lens power supply source 9. According to embodiments of the present invention, a spherical aberration corrector 10 as described above also is included in the system. The electron microscope 1 also comprises a detection system 11, the detected information being applied to an image processing system 13. The electron beam 15 is incident on an object 17. High-resolution images of the object 17 can be recorded in images planes 19 with slightly different defocus values. In practice, the beam is generated by the source 3 and goes through the sample. Thereafter, the beam goes through the objective lens. In embodiments of the present invention the spherical aberration corrector is embedded in the objective lens. After the beam has passed the objective lens, the beam goes through the aperture, positioned in the focal plane of the objective lens. Thereafter the beam is imaged by the projector lens (not shown) on to the image plane where the detection system is located.

In a particular embodiment, the system furthermore comprises an annular dark field objective aperture 31 for selecting in this way the thermal diffuse scattered electrons. The annular dark field objective aperture 31 has an annular ring shape with an inner radius and an outer radius, the inner and the outer radius selected corresponding with the frequency band of the thermal diffuse scattered of electrons scattered at a soft matter object. Although embodiments without annular aperture are also envisaged, such embodiments render the imaging more difficult as there is a coherent contribution.

The system according to embodiments of the present invention also may comprise a controller for performing tomographic processing according to methods as described in the present invention.

In one aspect, the present invention also relates to an image processor 13 as such for performing processing steps used in or according to method embodiments as described above.

In yet another aspect, the present invention relates to an annular dark field objective aperture for use in an electron microscopy system. The annular dark field objective aperture thereby comprise an annular ring shaped aperture, with an inner radius and an outer radius, whereby the inner and the outer radius are selected such that thermal diffuse scattered electrons are selected for detection in the electron microscopy system. The inner and the outer radius thus may be selected so that the aperture corresponds with the frequency band of the thermal diffuse scattered electrons scattered at a soft matter object. Such a range may correspond with a part or all of the range between 0.5 Å$^{-1}$ and 1.0 Å or may comprise a part thereof.

In still another aspect, the present invention relates to the use of a system as described above for performing imaging of a soft matter object, e.g. a biological object. The electron microscope images obtained through the use or by applying the method also fall within the scope of the present disclosure.

Without wishing to be bound by theory, features and aspects of embodiments of the present invention can be based on the following theoretical considerations, embodiments of the present invention not being limited thereby.

First, conventional accepted basic theoretical principles for imaging a phase object are discussed.

Start from the assumption that a single atom acts as a phase object, the wavefunction, after transmission of the atom, is $$\psi(r) = e^{iV(r)} \tag{1}$$

where V(r) is (apart from the proportionality constant) equal to the projected electrostatic potential of the atom. r is taken in the plane of projection.

Equation (1) is then expanded up to second order. For simplicity the real space vector r is omitted $$\psi = 1 + iV - \frac{V^2}{2} \tag{2}$$

After transmission through the electron microscope, the wave function in the image plane is then $$\psi_{im} = \psi * T \quad (3)$$

With T the complex point spread function of the electron microscope, which is the Fourier transform of the transfer function. From (2) and (3) one has $$\psi_{im} = 1 + iV * T - \frac{V^2}{2} * T \quad (4)$$

and for the image intensity one has $$I(r) = |\psi_{im}|^2 = 1 - 2V*(Im\ T) - V^2*(Re\ T) + (V*T)^2 \quad (5)$$

Where Im T and Re T are the imaginary respectively real part of T.

The coherent transfer function of an electron microscope is given by equation (4).

$$T(g) = e^{-i\chi(g)} \quad (6)$$

with $$\chi(g) = \frac{\pi}{2}(C_s \lambda^3 g^4 + 2\varepsilon\lambda g^2) \quad (7)$$

With $C_s$ being the spherical aberration constant, $\lambda$ the electron wavelength, g the spatial frequency and $\varepsilon$ the defocus.

$$Im\ T(g) = \sin \chi(g)$$

$$Re\ T(g) = \cos \chi(g)$$

It is very convenient to express $\chi(g)$ in dimensionless units by writing g in units Glaser $$1 Gl = C_s^{1/4} \lambda^{1/4} \quad (8)$$

and the defocus $\varepsilon$ in Scherzer units $$1 Sch = C_s^{1/2} \lambda^{1/2} \quad (9)$$

so that $$\chi(g) = \frac{\pi}{2}(g^4 + 2\varepsilon g^2) \quad (10)$$

In high resolution electron microscopy HREM, the phase shift due to spherical aberration is partly compensated by underfocusing the electron microscope. The optimum defocus is $$\varepsilon = -1.22$$

Figure 2:
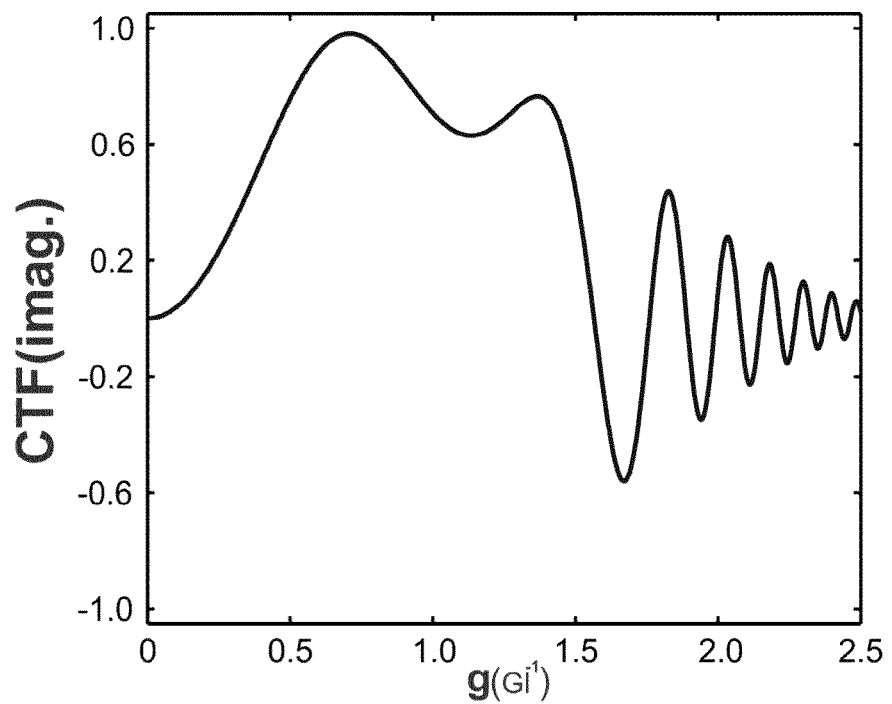
FIG. 2 illustrates the imaginary part of the transfer function at optimum defocus, illustrating comparative material as can be used for illustrating features of embodiments of the present invention

FIG. 2 shows the imaginary part of the transfer function Im(g) at optimum defocus. The spatial frequencies are expressed in Glaser$^{-1}$ units (1 Gl=$C_s^{1/4}\lambda^{1/4}$). The optimum defocus in this example is equal to 1.22 Scherzer units (1 Sch=$C_s^{1/5}\lambda^{1/2}$). For the temporal incoherence (damping envelope) it was assumed that there is a defocus spread of 0.1 Sch. The transfer function now shows a passband with a phase shift of about $\pi/2$. The FWHM of this passband extends approximately between $g_{min}$=0.5 and $g_{max}$=1.5 and the highest spatial frequency is then about g=1.6 which yields a resolution of 0.65 Gl.

For the spatial frequencies in the passband in Fourier space, we have approximately $$Im\ T(g) \approx 1$$

$$Re\ T(g) \approx 0$$

so that $$I = 1 - 2V + V^2 \quad (11)$$

Thus in first order the contrast directly reveals the projected electrostatic potential. Atoms should be black and holes white. However, below g=0.5, the low spatial frequencies are transmitted with low contrast. This is a drawback for imaging biological structures such as in single particle electron tomography of proteins, in which the low spatial frequencies carry most information about the real 3D structure of the object.

For a non-corrected HREM ($C_s$=3 mm) operated at 300 KeV at optimum focus the passband extends between 0.12 Å$^{-1}$ and 0.3 Å$^{-1}$.

However for a HREM with spherical aberration correction ($C_s$=10 μm) operated at optimum focus the passband extends between 0.5 Å$^{-1}$ and 1.6 Å$^{-1}$ This has conventionally lead to the conclusion that $C_s$ correction is useless for phase contrast electron microscopy.

Figure 3:
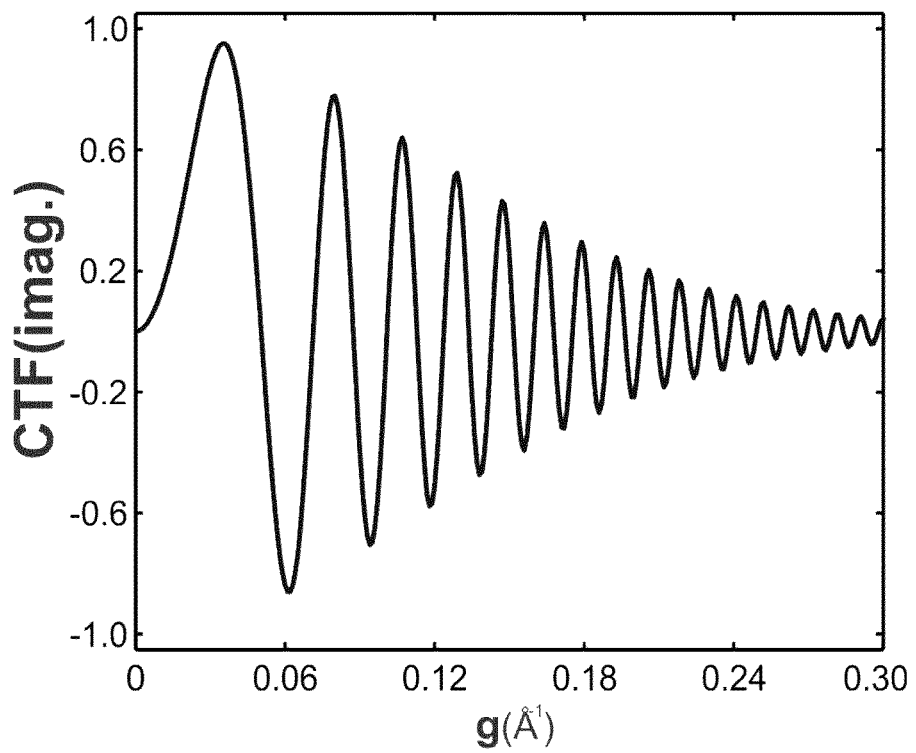
FIG. 3 illustrates the imaginary part of the transfer function at strong under focus, illustrating comparative material as can be used for illustrating features and advantages of embodiments of the present invention.
Figure 4A:
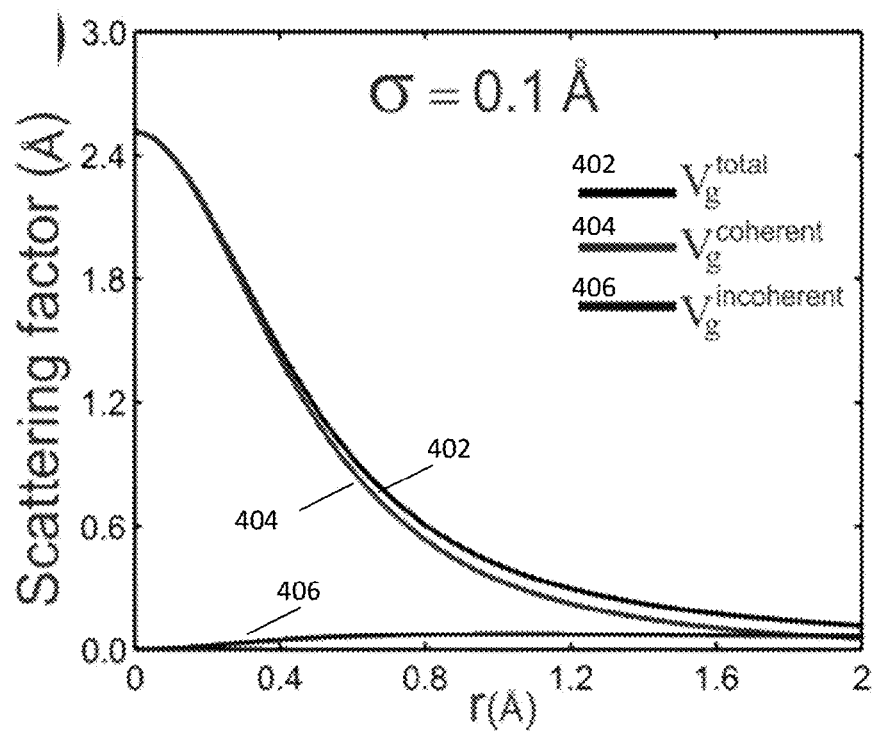
FIG. 4a to FIG. 4f illustrates the electron scattering factor contribution of a carbon atom, illustrating features as can be used in embodiment of the present invention.
Figure 4B:
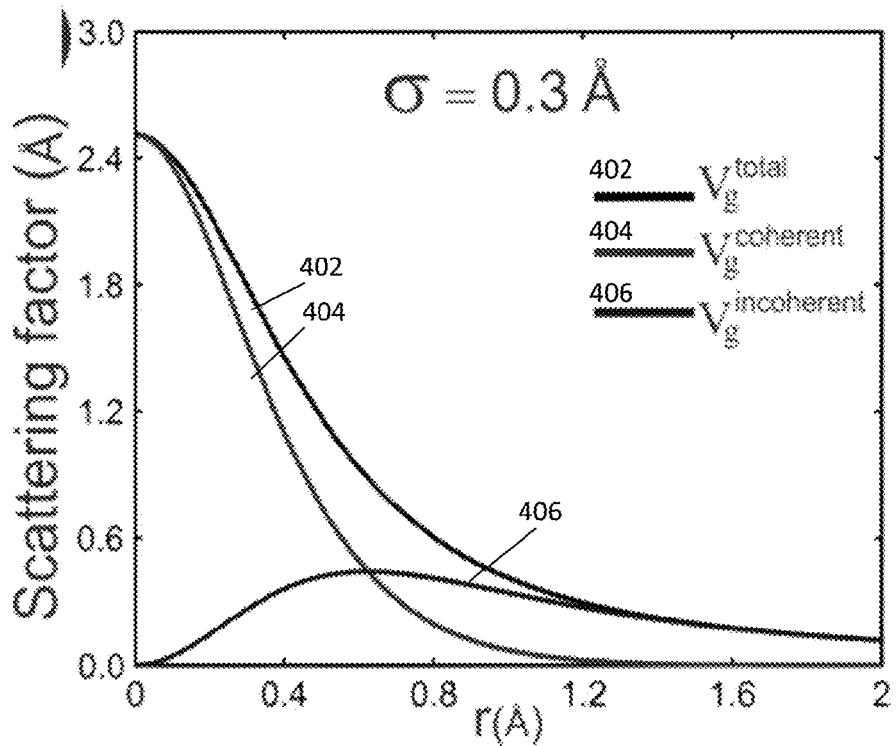
Figure 4C:
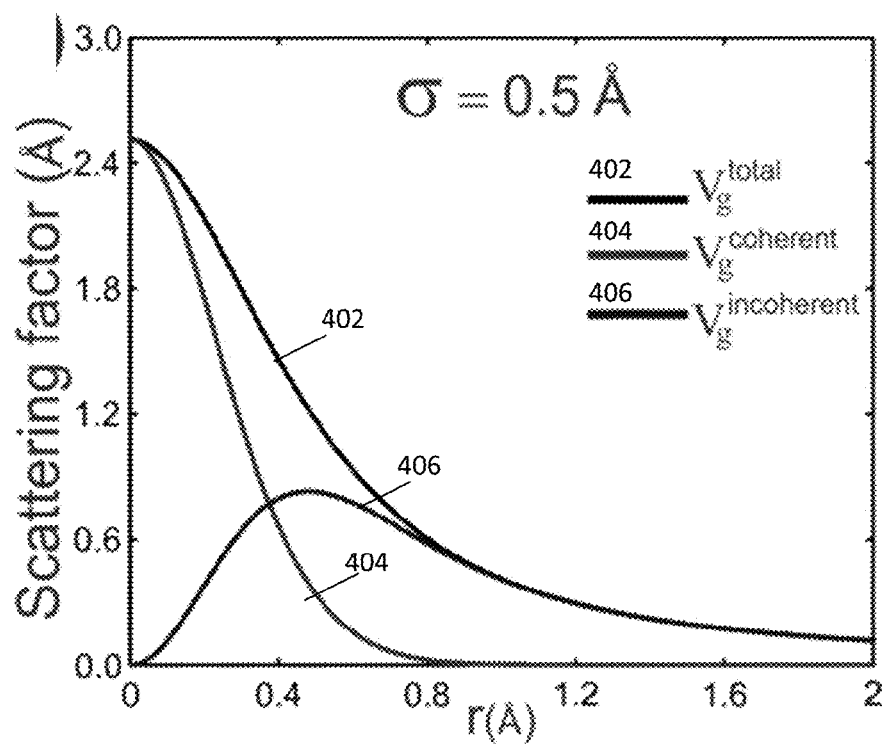
Figure 4D:
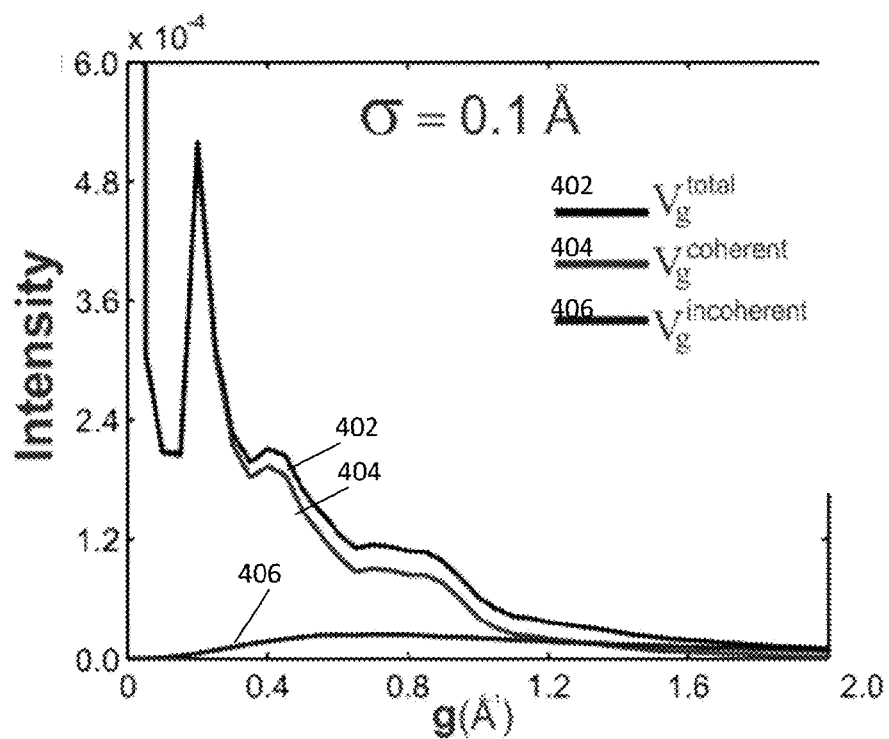
Figure 4E:
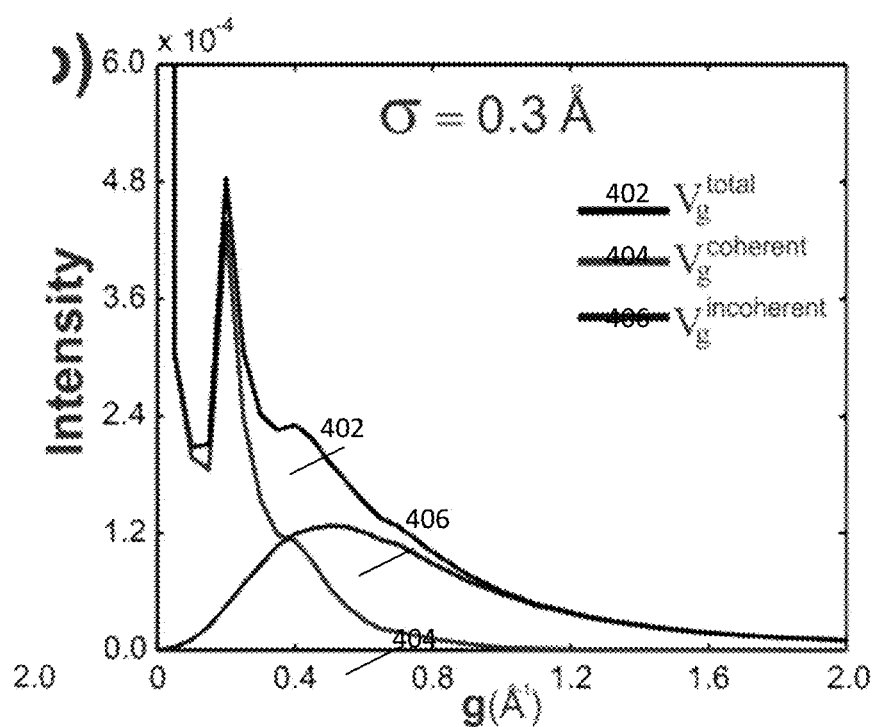
Figure 4F:
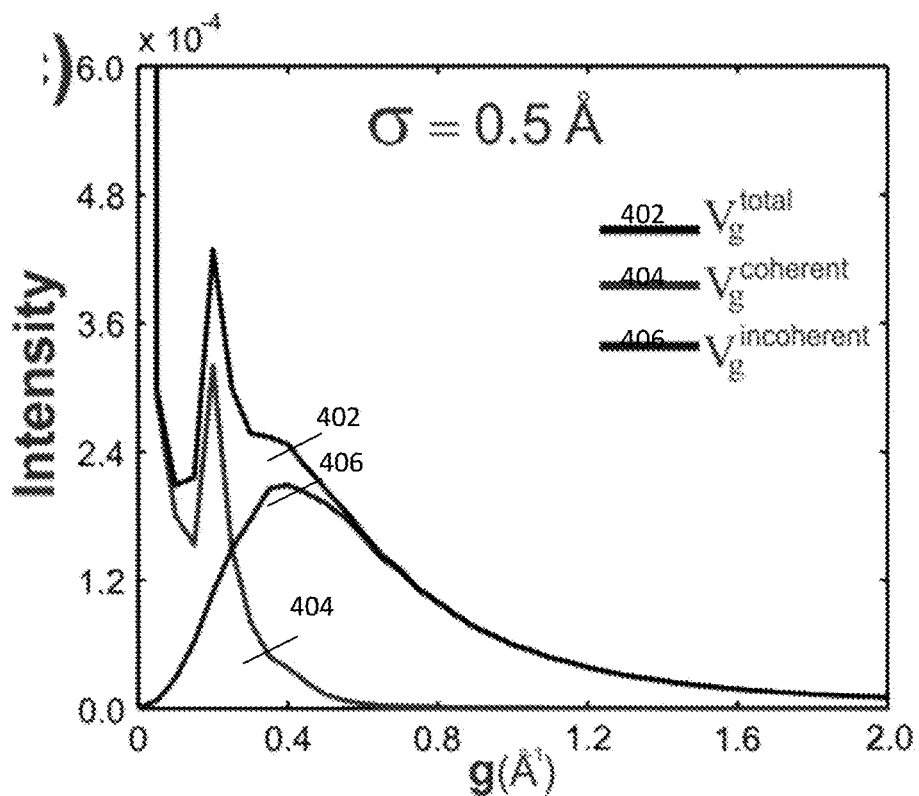

A common technique to increase the contrast is to use very large defocus values, as shown by way of example in FIG. 3. FIG. 3 illustrates the imaginary part of the transfer function Im(g) at strong underfocus of 20 Sch. This increases the contrast for the low spatial frequencies but at the expense of a loss at the high resolution end. A consequence thus is that the high resolution is lost especially due to the effect of spatial incoherence. For this reason it is generally believed that one cannot reach high resolution even with a $C_s$ corrected electron microscope.

An alternative is to develop an electrostatic phase plate that shifts the phase of the central beam over 90° (factor–i) so that $$\psi_{im} = -i + iV*T - \frac{V^2}{2}*T \quad (12)$$

and $$I \approx 1 - 2V*T \quad (13)$$

So that the contrast is again linear in the projected potential. But thus far no phase plate are demonstrated that work reliably for high resolution phase contrast.

The only correct way to include the spatial and temporal incoherence of the microscope is by averaging the image intensity over the different focus values within the focal spread and the different beam inclinations within the incident beam cone.

$$\langle I(r)\rangle_M = 1 - 2V*Im\langle T\rangle_M - V^2*Re\langle T\rangle_M + \langle |V*T|^2\rangle_M \quad (14)$$

In Fourier space, the averaging $\langle T\rangle_M$ gives rise to damping envelopes that reduces the higher spatial frequencies $$\langle T(g)\rangle_M = T(g) \cdot D_T(g) D_S(g) \quad (15)$$

where the damping envelope for temporal incoherence is given by $$D_T(g) \exp(-r^2 \lambda^2 \Delta^2 g^4) \quad (16)$$

With $\Delta$ the defocus spread and for spatial incoherence $$D_S(g) = \exp[-r^2 \alpha^2 [\nabla \chi(g)]^2] \quad (17)$$

with α the semi angle of the incident beam cone and ∇ the gradient of the phase with respect to the spatial frequency g.

In case of a large defocus (order of microns) the damping envelope of spatial incoherence is dominated by the defocus and becomes $$D_S(g) = \exp(-r^2 a^2 \epsilon^2 g^2) \tag{18}$$

which cuts the largest spatial frequency $$\left(\frac{1}{e} \text{ value}\right)$$

to $$g_{max} = \frac{1}{r\alpha\varepsilon} \tag{19}$$

In case of a very large defocus (2 micron) with beam divergence semi-angle 0.1 mrad we have $$g_{max} = 0.16 \text{ Å}^{-1} \tag{20}$$

Thus all the terms in (14) that are linear in T(g) are very strongly dampened.

That is the reason why it is believed that phase contrast by strong defocus cannot yield high resolution and cannot profit from Cs correction.
However, because $$\langle |V^*T|^2 \rangle_M \neq |V^* \langle T \rangle_M|^2 \tag{21}$$

these arguments do not hold for the nonlinear term in for which the highest spatial frequencies are not necessarily reduced.

What happens in practice is that the information can leak trough the large spatial frequencies of T to contribute to the image intensity. And this intensity does not disappear when averaging afterwards. However if the electron microscope is strongly defocussed this information is strongly delocalized into the background of the image. But if the electron microscope is operated at optimal defocus and with allow Cs one can shift the passband exactly to these spatial frequencies so as to image this nonlinear contribution with high resolution.

And since this term is added incoherently we can generate amplitude contrast without the need for a phase shift of $$\frac{\pi}{2}.$$

It is sufficient that the phase shift in the passband is approximately constant. It should be noted that the nonlinear contribution also contributes to the low spatial frequencies as required to image biological objects.

In reality, the atoms of the object are not still but they oscillate around an average position during the recording of the image. It is generally believed that this reduces the large angle scattering and thus also the high spatial frequencies so as to have only a minor influence on the image contrast.

As will be described below, large angle scattering and thus also the high spatial frequencies have a significant influence on the image contrast.

Let us for simplicity consider the case of one particular atom with projected electrostatic potential V(r).

In Fourier space the scattering factor of the still atom V(g) is given by the Mott-Bethe formula $$V(g) = \frac{Z - f_x(g)}{g^2} \tag{22}$$

Note that the "tail" of this factor decreases only slowly with increasing g, which is a consequence of the singularity of the electrostatic potential of the nucleus of the atom. Since the atom vibrates around its equilibrium position we can define a kind of averaged potential $$\langle V(r) \rangle = V(r) * P(r) \tag{23}$$

Where P(r) is the position distribution of the atom position. ⟨ ⟩ stands for average over the different atom positions. Fourier transforming then yields $$\langle V(g) \rangle = V(g) \cdot P(g) \tag{24}$$

In case the position distribution function is Gaussian with mean square displacement σ we have $$P(r) = \frac{1}{\pi\sigma^2} e^{-\frac{r^2}{\sigma^2}} \tag{25}$$

Its Fourier transform P(g) is also Gaussian.

$$P(g) = e^{-\pi^2 \sigma^2 g^2} \tag{26}$$

In Fourier space the scattering factor of the atom V(g), is then multiplied by a Gaussian "Debye-Waller" factor.

$$\langle V(g) \rangle = \left(\frac{Z - f_x(g)}{g^2}\right) e^{-\pi^2 \sigma^2 g^2} \tag{27}$$

The error that is usually made in electron diffraction theory is that the electron scattering factors of the atom are also systematically multiplied by Debye-Waller factors as if the atoms are replaced by their thermal average. This approximation has been borrowed from X-ray diffraction where all the atoms of a crystal lattice constructively interfere linearly in the diffracted wave (Fourier transform). And since this linearity commutates with the linear averaging a diffracted beam "sees" a kind of averaged atom. However this approximation is not valid for electron diffraction. Indeed every electron sees a still atom (frozen atom) and the averaging over the different atom positions has to be done at the level of the detection of the images or diffraction patterns. Since the atom has a very sharp potential in its center the electron will scatter appreciably at high angles. This high angle scattering does not disappear on averaging. If on the other hand the atom is "blurred" by a Debye Waller factor, the high angle scattering is artificially reduced so that the thermal diffuse scattering is underestimated.

In case of a perfect crystal ⟨V(r)⟩ reveals the crystal symmetry and ⟨V(g)⟩² then reveals the Bragg peaks in the diffraction pattern. The nonlinear term, which violates the crystal symmetry, generates a diffuse intensity background. Hence the term thermal diffuse scattering (TDS).

FIG. 4a to FIG. 4f illustrates the electron scattering factor contribution of a Carbon atom whereby total 402, coherent 404 and incoherent 406 electron scattering contributions for different RMS are given. FIG. 4a to FIG. 4f shows a plot of V(g), ⟨V(g)⟩ and V(g)−⟨V(g)⟩ for various values of σ, i.e. for σ=0.1 Å, for σ=0.3 Å, σ=0.5 Å. For very low σ (0.1 Å), which is typical for inorganic crystals, the incoherent contribution is relatively small and distributed over a very large area in Fourier space. However, for very large σ (0.5 Å) as typical for soft matter, the incoherent contribution is comparable to the coherent contribution and peaked at relatively low spatial frequencies (0.5 Å$^{-1}$).

The total incoherent (TDS) intensity is given by I=C σ$^2$Z$^2$ which is not only proportional to Z$^2$ but also to the mean square displacement σ$^2$ of the atom so that it can be important even for light atoms in soft matter.

Returning to the expression (6) of the image intensity.

When the image intensity is averaged, over the different atom positions $\langle \ \rangle_A$, one obtains $$\langle\langle I\rangle_M\rangle_A = 1 - 2\langle V\rangle_A * Im\langle T\rangle_M - \langle V^2\rangle_A * Re\langle T\rangle_M + \langle\langle |V \times T|^2\rangle_M\rangle_A \quad (28)$$

From (23) one has $$\langle V\rangle_A = V * P \quad (29)$$

and hence $$\langle V\rangle_A * \langle T\rangle_M = V * P * \langle T\rangle_M \quad (30)$$
$$= V * \langle P * T\rangle_M$$
$$= V * \langle\langle T\rangle_M\rangle_A$$

so that $$\langle\langle I\rangle_M\rangle_A = 1 - 2V * Im\langle\langle T\rangle_M\rangle_A - V^2 * Re\langle\langle T\rangle_M\rangle_A + \langle\langle |V*T|^2\rangle_M\rangle_A \quad (31)$$

Combining (15) with (26) gives $$\langle\langle T(g)\rangle_M\rangle_A = T(g)D_T(g)D_S(g)P(g) \quad (32)$$

If one would operate the electron microscope in high resolution mode with low Cs and at optimum focus, the combination of the reduction of the low spatial frequencies in sin $\langle T(g)\rangle$ with the damping envelopes will significantly reduce the contribution of the term Im$\langle\langle T\rangle\rangle$ in (32) especially for atoms in biological objects with large mean displacement.

The term V$^2$*Re$\langle T\rangle$ in (14) will then contribute to the low spatial frequencies but due to the strong damping of P(g) the high spatial frequencies will still be suppressed.

The term $\langle\langle |V \times T|^2\rangle_M\rangle_A$ however can still give very high resolution contrast.

This can be seen as follows:
Defining $$W(r) = V(r) - \langle V(r)\rangle \quad (33)$$

so that $$\overline{W(r)} = 0 \quad (34)$$

In Fourier space this is $$W(g) = V(g) - \langle V(g)\rangle \quad (35)$$

which, as discussed above, represents the thermal diffuse scattering.

One now has $$\langle\langle |V \times T|^2\rangle\rangle_{M,A} = |\langle V(r)\rangle_A * T|^2 + \langle\langle |W \times T|^2\rangle\rangle_{M,A} \quad (36)$$
$$= \langle |\langle V(r)\rangle_A * P * T|^2\rangle_M + \langle\langle |W \times T|^2\rangle\rangle_{M,A}$$

The first term is still limited to lower spatial frequencies because of the damping envelope P(g), although the convolution broadens the frequency band.

However the second term is much more important at high spatial frequencies. Indeed since W is the contribution of the TDS electrons it still scatters at very large angles.

Figure 5:
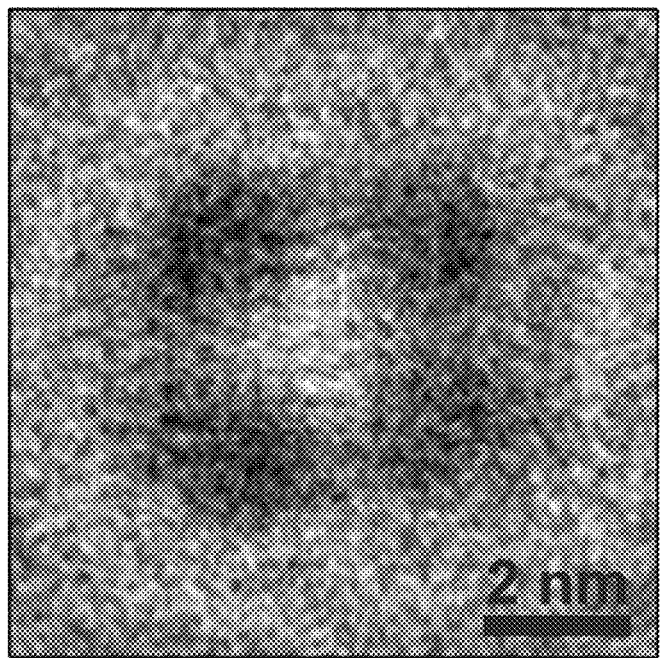
FIG. 5 to FIG. 7 illustrates a frozen image calculation of a complex, illustrating features of embodiments of the present invention.

FIG. 5 shows that this contribution is peaked around g=1 Å$^{-1}$. FIG. 5. Illustrates a frozen atom image calculation of a complex Δf=0.0, Δ=0.0, α=0.0. Total (black curve), elastic (red curve) and inelastic (blue curve) rotationally averaged power spectra for different RMS: a) σ=0.1 Å, b) σ=0.3 Å and c) σ=0.5 Å·Δf=10.9 nm).

The information of W*T can still be delocalized in the image. However since this delocalization is proportional to the gradient of the phase transfer χ(g), it can be minimized by keeping χ(g) constant over the frequency band W(g) of the TDS electrons so that the contribution of $\langle\langle |W \times T|^2\rangle\rangle_{M,A}$ can yield very high resolution.

It is possible to select only the contribution $\langle\langle |W \times T|^2\rangle\rangle_{M,A}$ This can be done by using an annular dark field aperture, and choosing the inner and outer radius so as to match the frequency band of the TDS contribution and by matching the phase transfer function that the phase is approximately constant over this band.

The optimal radii are dependent on the mean square displacement of the atoms of the object. But it can be expected that this band is located somewhere between 0.5 Å$^{-1}$ and 1.0 Å$^{-1}$ which requires the use of a Cs corrector.

Figure 6:
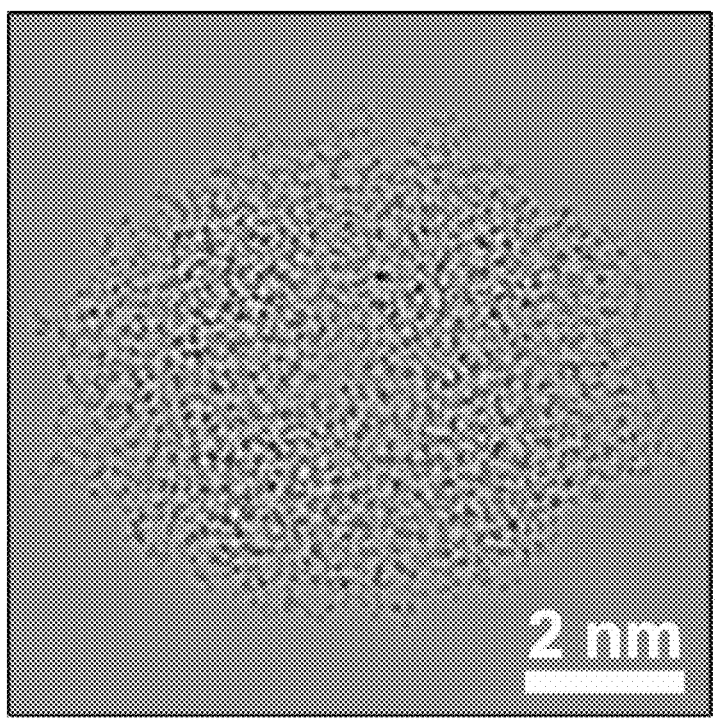
Figure 7:
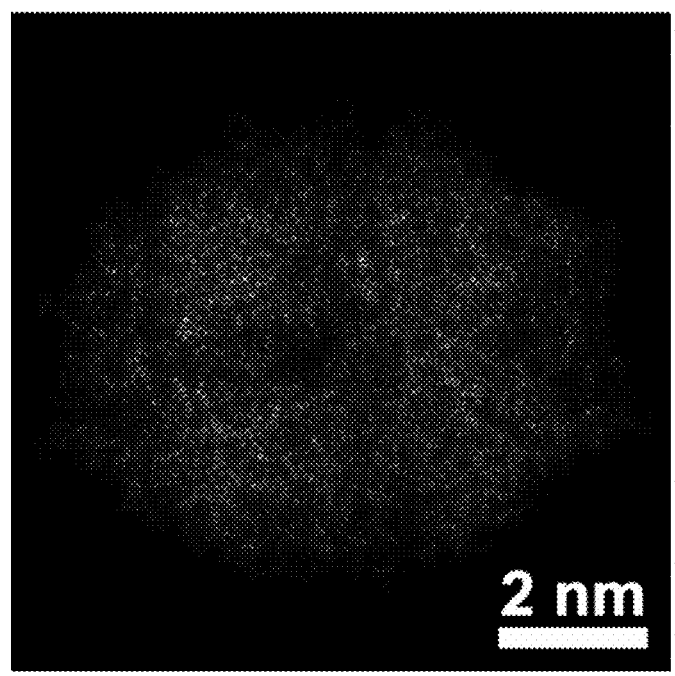

FIGS. 6 and 7 show simulations of the bright field respectively dark field images of aHbpS complex. From this it is clear that dark field ADF amplitude imaging yields both high contrast and atomic resolution. For FIG. 6 the electron microscope parameters used are acceleration voltage (E0=300 KeV), defocus spread (=3.2 nm), semi-convergence angle mrad), Spherical aberration (C$_s$=0.04 mm) and defocus (f=10.9 nm). The defocus spread (temporal incoherence) is correctly treated by adding the image intensities at the different defocus values. For FIG. 7, where the frozen atom image calculation using an annular dark-field aperture (g$_{min}$=0.5 Å$^{-1}$, g$_{max}$=2.0$^{-1}$) is shown, the electron microscope parameters used are acceleration voltage (E0=300 KeV), defocus spread (=3.2 nm), semi-convergence angle mrad), Spherical aberration (C$_s$=0.04 mm) and defocus (f=10.9 nm). The defocus spread (temporal incoherence) is correctly treated by adding the image intensities at the different defocus values.

For an assembly of atoms, so that one has $$W(r, t) = \sum_i W_i(r - r_i, t) \quad (37)$$

Let us call $\psi_i(r,t)$ the TDS part of the image wave of the atom $$\psi_i(r,t) = (r,t) * T(r) \quad (38)$$

From (22) one has $$\langle\psi_i\rangle = \langle W_i\rangle * T(r) = 0 \quad (39)$$

For the intensity one now has $$|\psi(r, t)|^2 = \sum_{i,j} \psi_i(r - r_i, t)\psi_j^*(r - r_j, t) \quad (40)$$

$$\langle|\psi(r, t)|^2\rangle = \left\langle\sum_{i,j} \psi_i(r - r_i, t)\psi_j^*(r - r_j, t)\right\rangle \quad (41)$$

and assuming independent atom motions (Einstein model) one has $$\langle \psi_i \psi_j \rangle = \langle \psi_i \rangle \langle \psi_j^* \rangle \quad (42)$$
$$= 0 \text{ if } i \neq j$$
$$= \langle \psi_i^2 \rangle \text{ if } i = j$$

So that $$I_{TDS}(r) = \sum_i \langle |\psi_i|^2 \rangle \quad (43)$$

The incoherent contribution of each atom is then independently added to the final image.

This result simplifies the interpretation of the high resolution images and it is very suitable for tomographic reconstruction algorithms.

In one embodiment, it is taken into account that in a usual projection approximation, it is assumed that every atom has the same contribution to the image but that in a 3D object, the atoms have a different vertical position and thus a slightly different defocus. As required from (34), the passband has to be roughly constant over the incoherent peak (FIG. 3). As follows from the above, the passband can allow for some shift in defocus of the order of $\Delta\epsilon=0.5$ Sch. For $C_s=10 \mu m$ 300 KeV at optimum defocus we then have $\Delta\epsilon=2$ nm. However, since the incoherent intensity peaks at about 0.5 $Å^{-1}$ we can use $C_s=100 \mu m$ and then $\Delta\epsilon=6$ nm, so that the requirement is still fulfilled for particles up to 12 nm thick. If this condition is not met, one can correct for this defocus effect in a second run of the tomographic scheme.

It was shown that it is possible to obtain high resolution images using TDS electrons. The image contrast is amplitude contrast. The contrast can be very high, even for soft matter. When the imaging is done with a flat transfer function, using a small defocus and a Cs corrected electron microscope and an appropriate aperture, the resolution can approach the limits of the electron microscope. Furthermore every atom contributes its own image intensity independently which makes the images easy to interpret and suitable for tomographic schemes.

Further by way of illustration, an example of thermal diffuse scattering is now discussed. The examples shows that the signal of TDS electrons of soft matter can be relatively large because it is not only function of the atomic number of the atoms but also of the mean square displacement (MSD). TDS scattering is incoherent and thus does not interfere with the central beam so that it generates amplitude contrast and it is maximal at a spatial frequency at which the phase transfer function can be made flat by combining a very low Cs with a small underfocus so as to get the highest resolution. Furthermore, the TDS signal is linear in the "mass-thickness" and easy to interpret and so that is it very suited for tomography. It is also proposed to use an annular dark field objective aperture that is specially optimized for this imaging technique. In a sense the method is then comparable to HAADF STEM but with all the advantages of HREM.

Figure 8A:
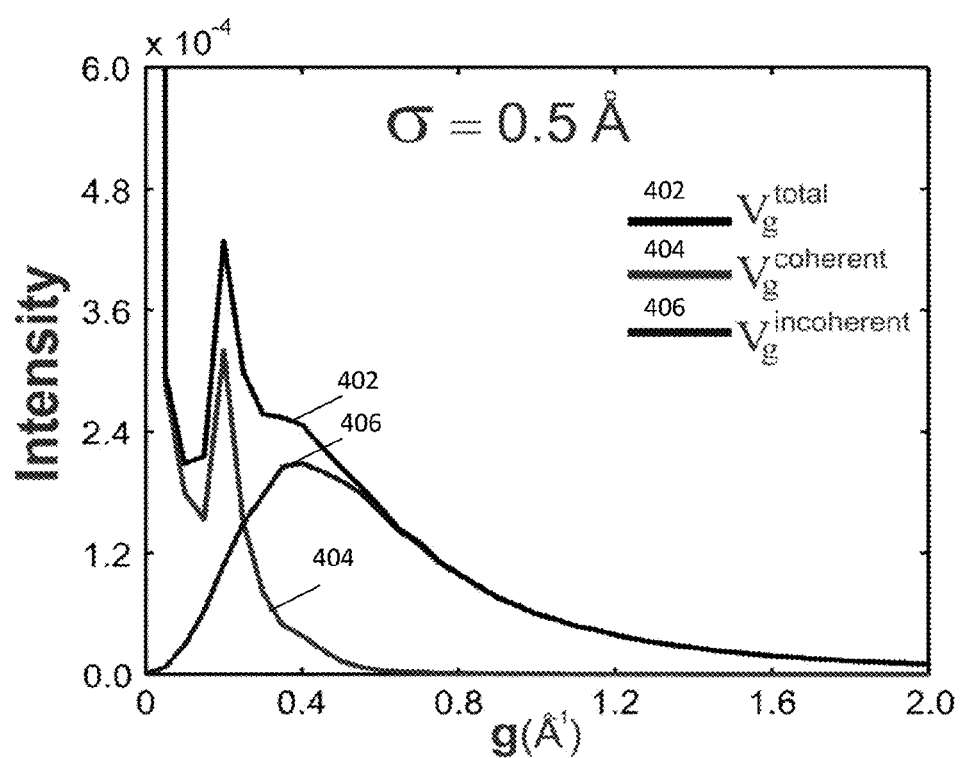
FIG. 8a, FIGS. 8b and 9 illustrate an example of a frozen image calculation of a complex with annular dark-field aperture, illustrating features of embodiments of the present invention.
Figure 8B:
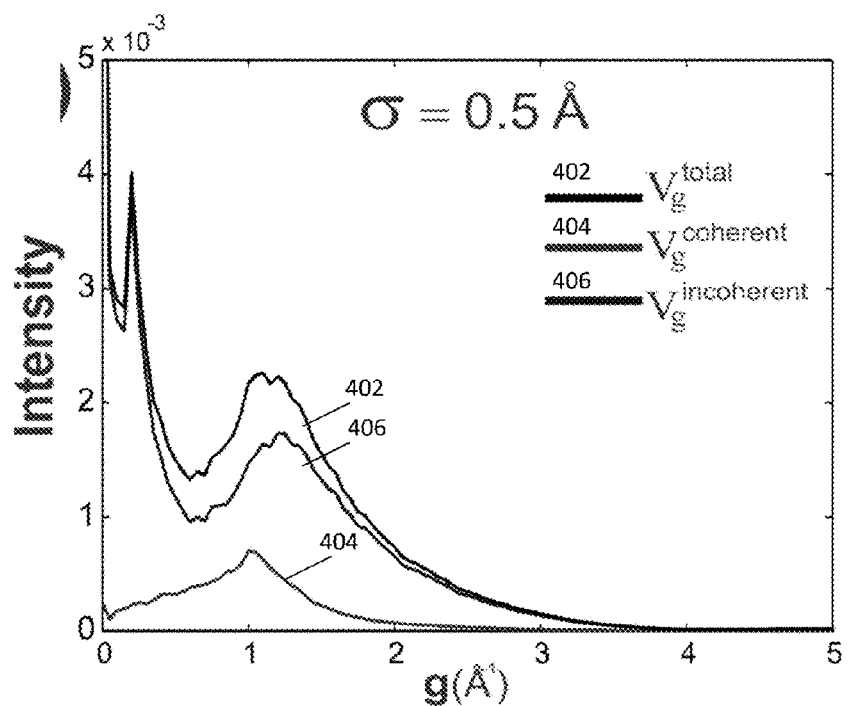

In a real object the atoms are not still but they vibrate around an average position. It is generally believed that can be described properly using a Debye Waller factor, which reduces the scattering at large angles scattering with only a minor influence on the image contrast. However this is a misconception which can even be exploited favorably for imaging purposes. Let us consider the imaging of a single atom that vibrates around its equilibrium position. In the weak phase approximation the HREM image intensity of a single atom is given by $$\langle \langle I \rangle_M \rangle_A = 1 - 2 \langle V \rangle_M * \text{Imag} \langle T \rangle_M - \langle V^2 \rangle_A * \text{Real} \langle T \rangle_M + \langle |\langle V \rangle_A * T|^2 \rangle_M + \langle \langle |W*T|^2 \rangle_M \rangle_A$$

Where V is the atom potential, $W=V-\langle V\rangle$ describes the TDS due to the atom displacement, T is the point spread function of the microscope. * stands for convolution and $\langle\rangle_A$ for averaging over the atom positions. $\langle\rangle_M$ stands for averaging over the microscope incoherences thus causes a damping envelope of the linear terms in $\langle T\rangle$ so as to reduce the resolution especially for atoms with large mean displacement as in biological objects. On the other hand the nonlinear TDS contribution of W*T can still give a strong signal at large spatial frequencies although. Because of the phase oscillations in T it can be delocalized in the image. However this delocalization can be minimized by shifting the passband of the transfer function till this spatial frequency which as shown in FIG. 8a and FIG. 8b is peaked around g=1 $Å^{-1}$. Signals representative for the total signal 402, the coherent signal 404 and the incoherent signal 406 are indicated.

Figure 9:
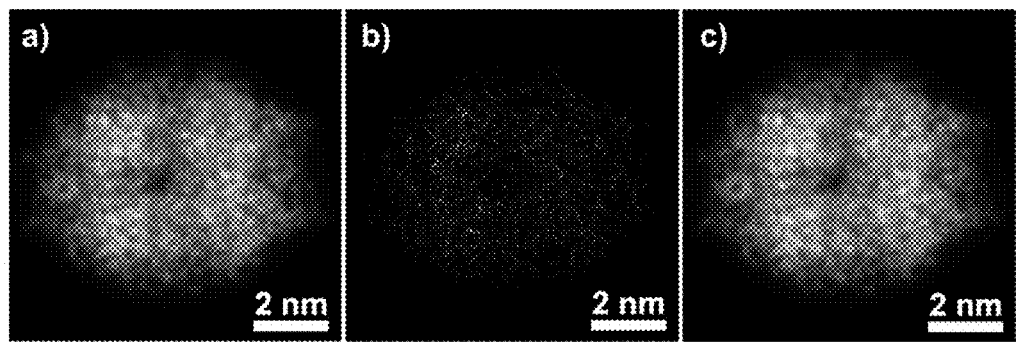

It is possible to select only the TDS signal by using an annular dark field aperture[2], which matches the TDS contribution and by optimizing Cs and defocus so that the phase is approximately constant over this peak. FIG. 8a and FIG. 8b shows the rotationally averaged power spectras of an HbpS complex. FIG. 8a shows a diffraction pattern at 300 KeV and FIG. 8b shows a diffractogram (E0=300 KeV, $\Delta$=3.2 nm, $\alpha$=0.2 mrad, $C_s$=0.04 mm and $\Delta f$=10.9 nm). FIG. 9 shows a simulation of dark field image of an HbpS complex a) Total, b) Coherent and c) incoherent intensities. From FIG. 8a, FIGS. 8b and 9 it is clear that, this TDS imaging mode yields both high contrast and atomic resolution. If we assume that the atom motions are uncorrelated (Einstein model) the TDS contribution of each atom is incoherently (independently) added to the final image which simplifies the interpretation of the high resolution images and it is very suitable for tomographic reconstruction algorithms. It is also possible to correct for slight differences in defocus of the atoms in the 3D object. In FIG. 8a and FIG. 8b a frozen atom image calculation of a complex HbpS with Annular dark-field aperture ($g_{min}=0.5$ $Å^{-1}$, $g_{max}=2.0^{-1}$) is shown. The following parameters are used: a) Diffraction at 300 KeV and b) Diffractogram for an electron microscope parameters (E0=300 KeV, $\Delta$=3.2 nm, $\alpha$=0.2 mrad, $C_s$=0.04 mm, $\Delta f$=10.9 nm). Total, coherent and incoherent rotationally averaged power spectra for RMS ($\sigma$)=0.5 Å are shown. FIG. 9 illustrates a frozen atom image calculation of a complex HbpS with Annular dark-field aperture ($g_{min}=0.5$ $Å^{-1}$, $g_{max}=2.0^{-1}$), whereby the following electron microscope parameters are used: acceleration voltage (E0=300 KeV), defocus spread ($\Delta$=3.2 nm), semi-convergence angle ($\alpha$=0.2 mrad), Spherical aberration ($C_s$=0.04 mm) and defocus ($\Delta f$=10.9 nm). a) Total intensity, b) Coherent intensity contribution and c) Incoherent intensity contribution.

The invention claimed is:
1. A method for performing high resolution electron microscopy of an object at atomic level resolution, the method comprising:
   irradiating a soft matter object using an electron microscope having a spherical aberration correction;
   detecting the thermal diffuse scattered electrons scattered at the object;

wherein the method comprises:
  irradiating the soft matter object by a coherent electron source;
  using the detected thermal diffuse scattered electrons for deriving therefrom an image of the object;
  wherein the spherical aberration correction has a substantially constant transfer function in a frequency band of thermal diffuse scattered electrons scattered at the object, within a tolerance margin in the order of micrometers.

2. A method according to claim 1, wherein the object is a soft matter object selected from the group consisting of proteins and polymers.

3. A method according to claim 1, wherein the frequency band of thermal diffuse scattered electrons scattered at the object comprises the range between 0.5 Å−1 and 1.0 Å−1.

4. A method according to claim 1, wherein the irradiating furthermore is performed using a small defocus.

5. A method according to claim 1, wherein irradiating using a small defocus comprises irradiating using a small underfocus.

6. A method according to claim 1, wherein the irradiating is performed using an annular dark field objective aperture.

7. A method according to claim 6, wherein imaging using an annular dark field objective aperture comprises imaging using an annular dark field objective aperture having a substantially annular ring shape, wherein the annular ring shape has an inner and an outer radius, the inner and the outer radius selected such that thermal diffuse scattered electrons are selected for detection in the electron microscopy system.

8. A method according to claim 1, wherein the object is a biological object.

9. A method according to claim 1, wherein said performing high resolution electron microscopy comprises performing tomography.

10. A method according to claim 1, wherein deriving an image comprises adding the incoherent contribution of each atom independently to the final image.

11. A method according to claim 10, wherein deriving an image of the object based on the detected thermal diffuse scattered electrons comprises deriving independent sub-images based on the incoherent contribution of each atom.

12. A method according to claim 1, wherein the method comprises tomographic imaging of particles of a three dimensional object, whereby particles having a different depth position in the object with respect to the imaging system resulting in a defocus smaller than a predetermined value, are imaged in the same imaging step using the same imaging conditions.

13. A method according to claim 12, wherein the method comprises imaging particles having a different depth position in the object with respect to the imaging system resulting in a defocus larger than a predetermined value, in a separate imaging step using different imaging conditions taking into account the different defocus value.

14. A system for performing high resolution electron microscopy of an object at atomic level resolution, the system comprising:
  an electron source;
  a spherical aberration corrector;
  a detector arranged for detecting the thermal diffuse scattered electrons scattered at the object;
wherein:
  the electron source is a coherent electron source;
  the spherical aberration corrector has a constant transfer function in a frequency band of thermal diffuse scattered electrons scattered at the object, within a tolerance margin in the order of micrometers;
  an image processor for using the detected thermal diffuse scattered electrons for deriving based thereon an image of the object.

15. A system according to claim 14, wherein the electron microscope has a substantially constant transfer function in range between 0.5 Å−1 and 1.0 Å−1.

16. A system according to claim 14, the electron microscope furthermore comprising an annular dark field objective aperture.

17. A system according to claim 16, wherein the annular dark field objective aperture has an annular ring shape with an inner radius and an outer radius, the inner and the outer radius selected such that thermal diffuse scattered electrons are selected for detection in the electron microscopy system.

18. Use of a system according to claim 14 for imaging a soft matter object.

19. Use according to claim 18, for imaging a biological object.

20. An electron microscope image obtained using a method according to claim 1.

\* \* \* \* \*